(12) United States Patent
Muller

(10) Patent No.: US 8,459,867 B2
(45) Date of Patent: Jun. 11, 2013

(54) X-RAY APPARATUS AND MEDICAL WORKSTATION

(75) Inventor: Michael Muller, Augsburg (DE)

(73) Assignee: KUKA Laboratories GmbH, Augsburg (DE)

(*) Notice: Subject to any disclaimer, the term of this patent is extended or adjusted under 35 U.S.C. 154(b) by 306 days.

(21) Appl. No.: 12/935,158

(22) PCT Filed: Mar. 30, 2009

(86) PCT No.: PCT/EP2009/053704
§ 371 (c)(1),
(2), (4) Date: Sep. 28, 2010

(87) PCT Pub. No.: WO2009/121822
PCT Pub. Date: Oct. 8, 2009

(65) Prior Publication Data
US 2011/0069818 A1 Mar. 24, 2011

(30) Foreign Application Priority Data
Mar. 31, 2008 (DE) .......................... 10 2008 016 414

(51) Int. Cl.
*H05G 1/02* (2006.01)
(52) U.S. Cl.
USPC ......................................... 378/196; 378/197
(58) Field of Classification Search
USPC ................................................ 378/196, 197
See application file for complete search history.

(56) References Cited

U.S. PATENT DOCUMENTS

| 4,894,855 | A | * | 1/1990 | Kresse ........................... 378/196 |
| 6,104,780 | A | * | 8/2000 | Hanover et al. ................. 378/92 |
| 6,200,024 | B1 | * | 3/2001 | Negrelli ......................... 378/197 |
| 6,435,715 | B1 | | 8/2002 | Betz et al. |
| 6,582,121 | B2 | * | 6/2003 | Crain et al. .................... 378/197 |
| 6,636,581 | B2 | * | 10/2003 | Sorenson ......................... 378/58 |
| 6,869,217 | B2 | * | 3/2005 | Rasche et al. ................. 378/197 |
| 7,282,882 | B2 | * | 10/2007 | Kitatsuji et al. .......... 318/568.11 |
| 7,401,977 | B2 | * | 7/2008 | Graumann et al. ........... 378/205 |

(Continued)

FOREIGN PATENT DOCUMENTS

| DE | 19611705 A1 | 10/1997 |
| EP | 0 220 501 A1 | 5/1987 |

(Continued)

OTHER PUBLICATIONS

European Patent Office; Search Report in International Patent Application No. PCT/EP2009/053704 dated Jul. 2, 2009; 4 pages.

*Primary Examiner* — Allen C. Ho
(74) *Attorney, Agent, or Firm* — Wood, Herron & Evans, LLP

(57) ABSTRACT

The invention relates to an X-ray apparatus and a medical workstation. The X-ray apparatus has a first robot (R1) and a second robot (R2). The first robot (R1) has a plurality of first axles, a first securing device and a first control device (17) designed to actuate the first axles of the first robot (R1) for a movement of the first securing device. The second robot (R2) has a plurality of second axles, a second securing device and a second control device (37) designed to actuate the second axles of the second robot (R2) for a movement of the second securing device. An X-ray source (RQ) is arranged on one of the two securing devices, and an X-ray receiver (RE) is arranged on the other securing device.

13 Claims, 4 Drawing Sheets

U.S. PATENT DOCUMENTS

Figure 1:
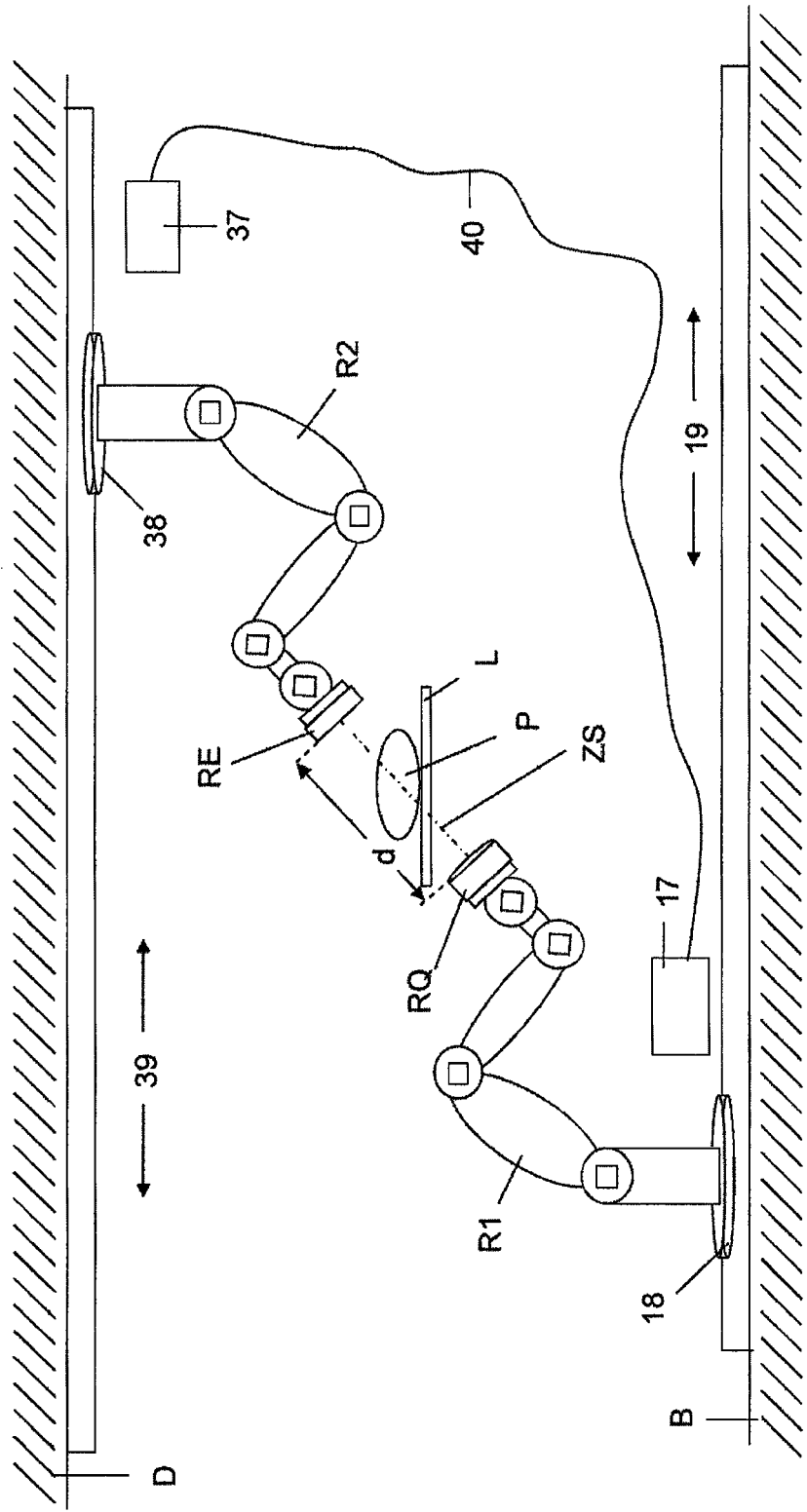

| | | | |
|---|---|---|---|
| 7,441,953 B2 * | 10/2008 | Banks | 378/197 |
| 7,530,739 B2 * | 5/2009 | Lurz et al. | 378/198 |
| 7,594,751 B2 * | 9/2009 | Grebner et al. | 378/197 |
| 7,724,870 B2 * | 5/2010 | Maltz et al. | 378/65 |
| 7,806,589 B2 * | 10/2010 | Tashman et al. | 378/197 |
| 2003/0091156 A1 | 5/2003 | Crain et al. | |

FOREIGN PATENT DOCUMENTS

| | | |
|---|---|---|
| EP | 0 699 794 A1 | 3/1996 |
| EP | 1 004 271 A1 | 5/2000 |
| EP | 1 106 141 A2 | 6/2001 |

\* cited by examiner

X-RAY APPARATUS AND MEDICAL WORKSTATION

The invention relates to an X-ray device and a medical workstation.

Robots in general are working machines, which can be equipped with tools for automatic handling and/or processing of objects, and are programmable in a plurality of motion axes, for example with regard to orientation, position and process sequence. Robots normally have programmable controllers (controlling devices) which control the sequences of motions of the robot during operation.

EP 1 106 141 A2 discloses a C-arm X-ray device having a C-arm, an X-ray source and an X-ray detector, each of which is situated at one end of the C-arm. The C-arm is situated on a supporting device in the form of a robot arm.

EP 0 220 501 B1 discloses an X-ray diagnostic system having a movable X-ray tube, a movable image recording system and a patient-transport trolley as system components, all of which are held by support arms. The support arms are constructed in the manner of robot arms, and the motors of the support arms are connected to a central computer which has means of storing various fixed positions and various program sequences for continuous motions of the system components.

The object of the invention is to specify a more flexibly constructed X-ray device which has an X-ray source situated on a first robot and an X-ray receiver situated on a second robot.

The problem of the invention is solved by an X-ray device having

- a first robot having a plurality of first axes, a first attaching device and a first control apparatus, which is set up to actuate the first axes of the first robot for a motion of the first attaching device,
- a second robot having a plurality of second axes, a second attaching device and a second control apparatus, which is set up to actuate the second axes of the second robot for a motion of the second attaching device,
- an X-ray source situated on one of the two attaching devices, and
- an X-ray receiver situated on the other attaching device, wherein the two control apparatuses are coupled together and are designed as a master-slave system wherein the first control apparatus is designed as the master and the second control apparatus is designed as the slave, the first control apparatus actuates the second control apparatus in such a way that at a first motion of the first attaching device the second control apparatus moves the second axes of the second robot in such a way that the second attaching device executes a second motion, on the basis of which the X-ray source and the X-ray receiver are constantly oriented relative to each other at a predefined distance.

Accordingly, the X-ray device according to the invention has two robots, each of which includes a plurality of axes, and each of which has an attaching device, in particular a flange. One of the robots is provided with the X-ray source and the other robot is provided with the X-ray receiver. In comparison to an X-ray device having a supporting device designed for example as a C-arm, to which the X-ray source and the X-ray receiver are attached and which is moved by a single robot, the individual supported load of the two robots of the X-ray device according to the invention is smaller.

Each of the two robots includes its own control apparatus. During operation of the X-ray device according to the invention, the respective control apparatuses actuate the axes of their respective robots. To that end, as is generally known to a person skilled in the art, the robots may be provided with electric drives, which are actuated in turn by the relevant control apparatuses. Hence the X-ray device according to the invention does not include a central control apparatus that actuates all of the axes of both robots together. As a result, it is possible to use two standard robots, each having a control apparatus intended for it. This can result in a more flexible embodiment of the X-ray device according to the invention.

In order for it to be possible to create X-ray images of an object using the X-ray device according to the invention, during operation the X-ray source and the X-ray receiver must be oriented relative to each other at the predefined distance. If the X-ray device according to the invention is also moved during operation, for example in order to produce a series of two-dimensional projections of the object, then it is also necessary during this motion for the X-ray source and the X-ray receiver, insofar as possible, to remain in a constant orientation relative to each other and to be at the predefined distance. In order to achieve this, the two control apparatuses are coupled together and are designed as a master-slave system. The first control apparatus is designed in this case as the master and the second control apparatus as the slave.

During operation of the X-ray apparatus according to the invention, it is therefore possible that the control apparatus designed as the master (the first control apparatus) actuates the control apparatus designed as the slave (the second control apparatus) during the first motion of the first attaching device of the first robot, so that the latter in turn actuates the second axes of the second robot in such a way that the second attaching device of the second robot follows the first motion of the first attaching device so that the X-ray source and the X-ray receiver are constantly oriented relative to each other at the predefined distance.

According to one embodiment of the X-ray device according to the invention, the first control apparatus controls the first axes of the first robot in such a way that the first attaching device executes the first motion. In order to realize this, a computer program runs for example on the first control apparatus, on the basis of which the first control apparatus for example actuates the aforementioned electric drives of the first robot, so that the first attaching device and thus also the X-ray source or the X-ray receiver, depending on which of the two component is attached to the first attaching device, automatically executes the first motion.

The X-ray device according to the invention can also have input means coupled with the first control apparatus, by means of which the first control apparatus actuates the first axes of the first robot in such a way that the first attaching device executes the first motion on the basis of a manual entry into the input means. Input means are for example a user interface coupled with the first control apparatus, by means of which for example a physician can bring the X-ray source to a desired position and orientation for an X-ray image. The X-ray receiver is then oriented automatically by means of the second robot so that it is oriented relative to the X-ray source at the predefined distance.

The X-ray device according to the invention can also be designed so that the first attaching device executes the first motion on the basis of a manual movement of the X-ray source situated on the first attaching device, or of the X-ray receiver situated on the first attaching device. Thus the X-ray device according to the invention can also be adjusted by guiding it manually. Because of the master-slave design of the two control apparatuses, the second control apparatus actuates the second attaching device in such a way that the latter automatically follows the manual motion (first motion) of the first attaching device.

The first motion can have a first linear motion component and/or a first circular motion component, and the second control apparatus can move the second axes in such a way that the second motion has a second linear motion component corresponding to the first linear motion component and/or a second circular motion component corresponding to the first circular motion component.

According to a variant of the X-ray device according to the invention, during the first motion the first control apparatus conveys to the second control apparatus information about the current position and orientation of the first attaching device, and the second control apparatus moves the second axes of the second robot on the basis of the relative location and orientation of the second robot relative to the first robot in such a way that the second attaching device has a position and orientation in which the X-ray source and the X-ray receiver are constantly oriented relative to each other at the predefined distance during the first motion. The second control apparatus according to this variant includes information about the relative location (position and orientation) of the two robots relative to each other. Based on the information about the location (position and orientation) of the first attaching device, it is possible for the second control apparatus to adjust the second axes of the second robot in such a way that the second attaching device is oriented relative to the first attaching device so that the X-ray source and the X-ray receiver are constantly oriented relative to each other at the predefined distance during the first motion. The relative locations of the two robots in relation to each other can be determined for example by surveying the two robots.

During the first motion, the first control apparatus can convey to the second control apparatus information about the current position and orientation of the X-ray source situated on the first attaching device or of the X-ray receiver situated on the first attaching device. On the basis of the relative location and orientation of the second robot in relation to the first robot and the information about the current position and orientation of the X-ray source situated on the first attaching device or of the X-ray receiver situated on the first attaching device, the second control apparatus can then move the second axes of the second robot in such a way that the second attaching device has a position and orientation in which the X-ray source and the X-ray receiver are constantly oriented relative to each other at the predefined distance during the first motion.

The first robot can have a first robot basic coordinate system and an attaching device coordinate system assigned to the first attaching device. The second robot can have a second robot basic coordinate system.

According to a variant of the X-ray device according to the invention, during the first motion the first control apparatus conveys to the second control apparatus information about the current position and orientation of the attaching device orientation system, and the second control apparatus moves the second axes of the second robot on the basis of the information about the position and orientation of the attaching device coordinate system and on the basis of information about the relative position and orientation of the two robot basic coordinate systems in relation to each other, in such a way that the second attaching device has a position and orientation in which the X-ray source and the X-ray receiver are constantly oriented relative to each other at the predefined distance during the first motion.

According to a variant of the X-ray device according to the invention, the X-ray source is situated on the first attaching device of the first robot and has a first X-ray source coordinate system, the X-ray receiver is situated on the second attaching device of the second robot and has a tool center point, the second control apparatus has access to information about the relationship between the first attaching device coordinate system and the X-ray source coordinate system, and the second control apparatus is set up to move the second axes of the second robot on the basis of the information about the position and orientation of the attaching device coordinate system, the information about the relationship between the attaching device coordinate system and the X-ray source coordinate system and on the basis of the information about the position and orientation of the two robot basic coordinate systems in relation to each other, in such a way that the tool center point is oriented so that the X-ray source and the X-ray receiver are constantly oriented relative to each other at the predefined distance during the first motion.

The X-ray source can also be situated on the second attaching device of the second robot and the X-ray receiver can be situated on the first attaching device of the first robot, in which case the X-ray receiver is assigned an X-ray receiver coordinate system and the X-ray source has the tool center point. If the second control apparatus has access to information about the relationship between the first control apparatus coordinate system and the X-ray receiver coordinate system, then the second control apparatus can be set up to move the second axes of the second robot, on the basis of the information about the position and orientation of the attaching device coordinate system, the information about the relationship between the attaching device coordinate system and the X-ray source coordinate system and on the basis of the information about the relative position and orientation of the two robot basic coordinate systems in relation to each other, in such a way that the tool center point is oriented so that the X-ray source and the X-ray receiver are constantly oriented relative to each other at the predefined distance during the first motion.

It is also possible, however, that the second control apparatus of the second robot moves the second axes of the robot directly on the basis of the information about the position and orientation of the X-ray source coordinate system or of the X-ray receiver coordinate system, in such a way that the X-ray source and the X-ray receiver are constantly oriented relative to each other at the predefined distance during the first motion.

The two robots can be set up freely in space. However, one of the robots or even both can also be suspended from a ceiling or from a wall.

One of the robots or both of the robots can also be movable by means of a linear unit, in particular a rail-bound linear unit. As a result, the working range of the relevant robot can be enlarged, whereby the flexibility of the X-ray device according to the invention can be increased.

The X-ray device according to the invention is intended in particular for a medical workstation which has a patient-transport trolley besides the X-ray device according to the invention.

Figure 2:
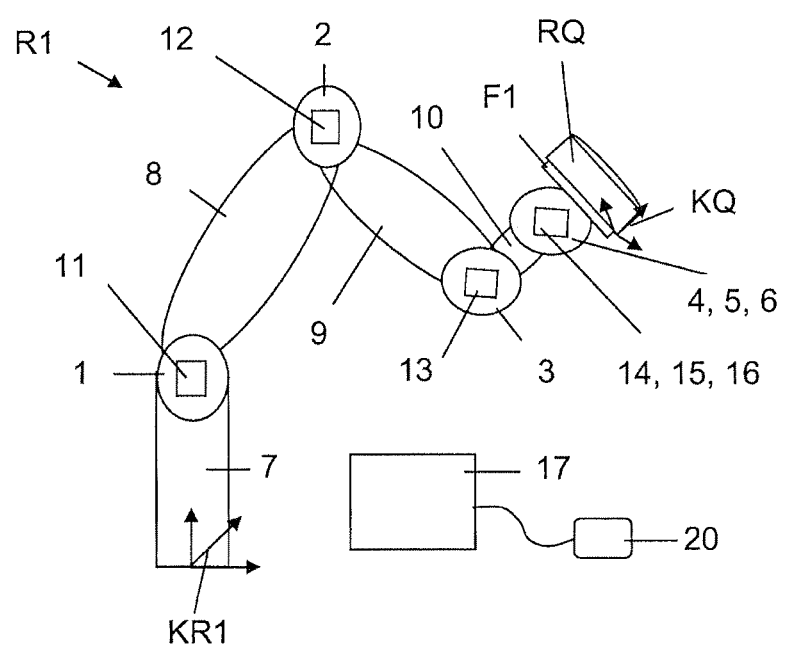
Figure 3:
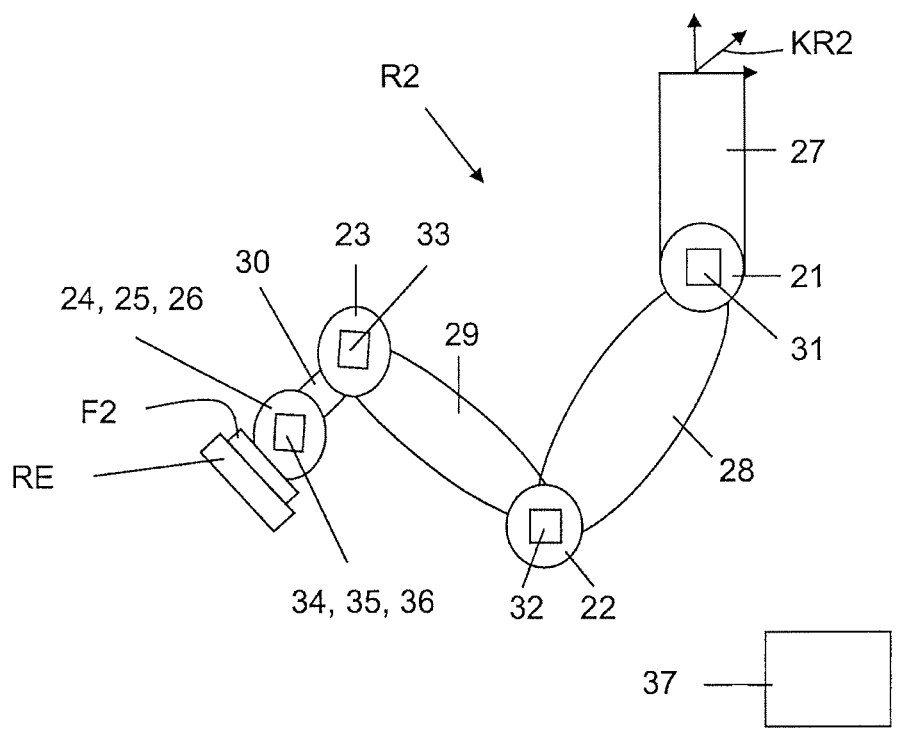
Figure 4:
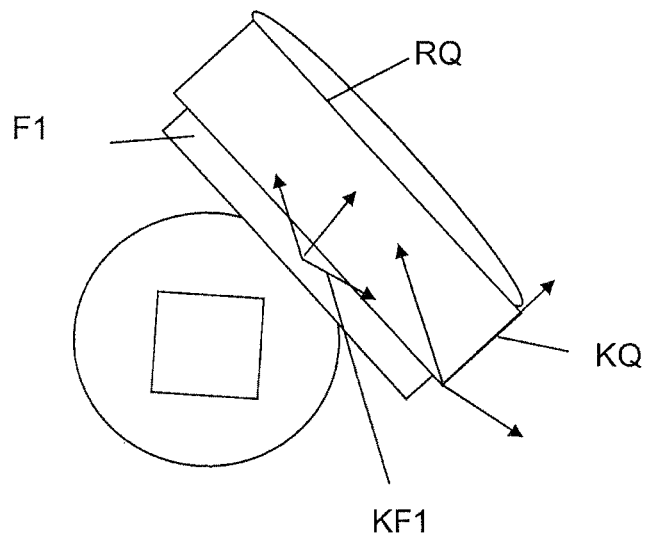
Figure 5:
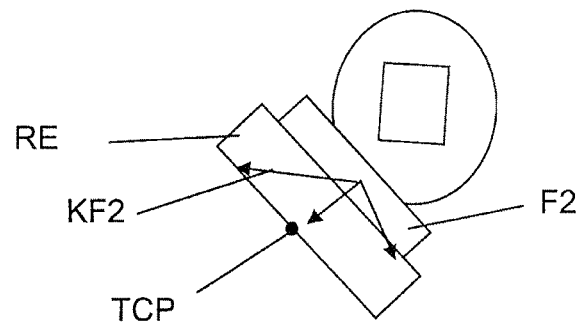

Examples of exemplary embodiments of the invention are depicted in the accompanying schematic drawing. The figures show the following:

FIG. 1 a medical work station,

FIG. 2 a first robot, to the flange of which an X-ray source is attached,

FIG. 3 a second robot, to the flange of which an X-ray receiver is attached, FIG. 4 the X-ray source attached to the flange of the first robot, and FIG. 5 the X-ray receiver attached to the flange of the second robot.

FIG. 1 shows a medical workstation having an X-ray device and a patient-transport trolley L, indicated only schematically, on which a person is lying for an examination using the X-ray device.

The X-ray device shown in FIG. 1 has a first robot R1, depicted in greater detail in FIG. 2, and a second robot R2, depicted in greater detail in FIG. 3.

The first robot R1 includes a plurality of axes 1-6, a plurality of levers 7-10, and a flange F1 to which an X-ray source RQ is attached. In the case of the present exemplary embodiment, each of the axes 1-6 is moved with an electric drive, which is electrically connected in a non-depicted manner to a control computer 17 of first robot R1, so that control computer 17 or a computer program running on control computer 17 is able to actuate the electric drives of first robot R1 in such a way that the position and orientation of flange F1 of first robot R1 can be oriented essentially freely in space. The electric drives of first robot R1 each include an electric motor 11-16 and possibly power electronics that actuate motors 11-16.

First robot R1 also has a robot coordinate system KR1, and flange F1 of first robot R1 has a flange coordinate system KF1 that is depicted in FIG. 4. In addition, X-ray source RQ has an X-ray source coordinate system KQ.

Second robot R2 includes a plurality of axes 21-26, a plurality of levers 27-30, and a flange F2 to which an X-ray receiver RE is attached. In the case of the present exemplary embodiment, each of the axes 21-26 is moved with an electric drive, which is electrically connected in a non-depicted manner to a control computer 37 of second robot R2, so that control computer 37 or a computer program running on control computer 37 is able to actuate the electric drives of second robot R2 in such a way that the position and orientation of flange F2 of second robot R2 can be oriented essentially freely in space. The electric drives of second robot R2 each include an electric motor 31-36 and possibly power electronics that actuate motors 31-36.

Second robot R2 also has a robot coordinate system KR2, and flange F2 of second robot R2 has a flange coordinate system KF2 that is depicted in FIG. 5. In addition, X-ray receiver RE has a tool center point TCP, and the two control computers 17, 37 are connected by means of a data line 40.

In the case of the present exemplary embodiment, first robot R1 is attached to a linear unit 18, which is attached to the floor B of the medical workstation and in particular is rail-bound, by means of which first robot R1 is movable along a double arrow 19. Second robot R2 is attached to a linear unit 38, which is attached to the ceiling D of the medical workstation and in particular is rail-bound, by means of which second robot R2 is movable along a double arrow 39. The two linear units 18, 38 each include drives, not depicted in the figures, the drive of first linear unit 18 being connected to control computer 17 of first robot R1 and the drive of second linear unit 38 being connected to control computer 37 of second robot R2. When robots R1, R2 are in operation, control computer 17 of first robot R1 controls linear unit 18 in order to move first robot R1 along double arrow 19, and control computer 37 of second robot R2 controls linear unit 38 in order to move second robot R2 along double arrow 39.

In the case of the present exemplary embodiment, in a first operating mode for example a physician, not depicted in further detail in the figures, is able to operate first robot R1 by means of a user interface 20 connected to first control computer 17 in such a way that first control computer 17 actuates the drives of first robot R1 so that flange F1 and thus X-ray source RQ executes a motion determined by the physician. Thus it is possible for the physician to orient the X-ray source RQ relative to person P in a desired manner in order to produce an X-ray image of a region of the body of person P.

For the X-ray image that the physician is able for example to trigger by means of an input means of user interface 20, not depicted in further detail, X-ray source RQ generates X-ray radiation having a central beam ZS.

For the recorded image, the X-ray is partially attenuated as it passes through person P, and strikes X-ray receiver RE. The latter converts the incident X-ray into an electrical signal corresponding to the X-ray, to which signal in turn an X-ray image of the relevant body region of person P, not depicted in further detail, is assigned. The X-ray image may be viewed for example by means of a display screen, not depicted in further detail for the sake of clarity.

So that the X-ray image will be of at least satisfactory quality, during the recording of the X-ray image the X-ray receiver RE should be oriented relative to X-ray source RQ at a predefined distance d. This is realized as follows in the case of the present exemplary embodiment:

The two control computers 17, 37 are designed as a master-slave system, control computer 17 of first robot R1 being designed as the master in the case of the present exemplary embodiment and control computer 37 of second robot R2 being designed as the slave. Based on the input into user interface 20, control computer 17 actuates the electric drives of first robot R1 and possibly of linear unit 18 in such a way that flange F1 of first robot R1 and thus X-ray source RQ execute the motion. At the same time, control computer 17 of first robot R1 conveys to control computer 37 of second robot R2 information about the current position and orientation of its flange F1, which in the case of the present exemplary embodiment represents information about the position and orientation of flange coordinate system KF1. Control computer 37 of second robot R2 also has access to information about the relative location (orientation and position) between flange coordinate system KF1 and X-ray source coordinate system KQ. Furthermore, the two robots R1, R2 were surveyed in advance, so that the second control computer 37 is also aware of information about the relative locations of the two robots R1, R2 in relation to each other, in particular the relative locations of the two robot coordinate systems KR1, KR2. Information about the current position of first robot R1, which is movable by means of linear unit 18, is likewise conveyed by control computer 17 of first robot R1 to control computer 37 of second robot R2 during the motion of flange F1 of first robot R1.

Hence it is possible for control computer 37 of second robot R2 to calculate the current position and orientation of flange F1 of first robot R1 or of X-ray source RQ, in order in turn to actuate the drives of second robot R2 by means of a computer program running on control computer R2 of second robot R2, in such a way that flange F2 of second robot R2 and in particular the tool center point TCP of X-ray receiver RQ is oriented so that the latter is at the predefined distance d from X-ray source RQ and is also aligned with the latter.

Control computer 17 of first robot R1 conveys the information described above to control computer 37 of second robot R2 continuously during the motion, so that control computer 37 of second robot R2 is constantly able to actuate the drives of second robot R2 so that X-ray receiver RE is constantly aligned with X-ray source RQ at distance d.

In the case of the present exemplary embodiment, the X-ray device can be operated in second operating mode. In the second operating mode, the physician is able to orient X-ray source RQ as desired, for example by means of user interface 20. Alternatively, it is also possible to orient X-ray source RQ as desired for example by guiding it manually. If X-ray source RQ is oriented as desired, then control computer 17 of first robot R1 conveys to control computer 37 of second robot R2 the information about the location of flange coordinate system KF1 and the position of first robot R1 with reference to linear unit 18. Control computer 37 of second robot R2 then actuates the drives of second robot R2 so that X-ray receiver RE is oriented relative to X-ray source RQ at distance d.

Next control computer 17 of first robot R1 actuates the drives of first robot R1 so that flange F1 of first robot R1, and thus X-ray source RQ, move in a circular arc, and in the case of the present exemplary embodiment traverse an angle of approximately 190°.

During this motion control computer 17 of first robot R1 continuously conveys information about the position and orientation of flange coordinate system KF1 and the position of first robot R1 with reference to linear unit 18.

Based on this information, control computer 37 is constantly aware of the location of X-ray source RQ during the motion of robot R1, and accordingly is able to actuate the drives of second robot R2 in such a way that the tool center point TCP of X-ray receiver RE is constantly oriented relative to X-ray source RQ at distance d so that X-ray source RQ and X-ray receiver RE are aligned with each other at distance d.

During the motions of X-ray source RQ and X-ray receiver RE around person P on a circular arc with an angle of about 190°, X-ray source RQ emits the X-ray radiation with a central beam ZS, so that X-ray receiver RE is able to create a series of 2-D image sets. It is then possible to compute from the 2-D image records in a generally known way a volume record of the body region of person P.

In the case of the present exemplary embodiment, the X-ray device can be operated in a third operating mode. In the third operating mode, the physician for example moves X-ray source RQ manually, for example by guiding or pulling on first robot R1 or on X-ray source RQ. During the manual motion, control computer 17 of first robot R1 continuously conveys information about the position and orientation of flange coordinate system KF1 and the position of first robot R1 with reference to linear unit 18.

Based on this information, control computer 37 is constantly aware of the location of X-ray source RQ during the manual motion of robot R1, and accordingly is able to actuate the drives of second robot R2 in such a way that the tool center point TCP of X-ray receiver RE is constantly oriented relative to X-ray source RQ at distance d so that X-ray source RQ und and X-ray receiver RE are aligned with each other at distance d.

In the described exemplary embodiments, control computer 17 of first robot R1 conveys information about the location of flange coordinate system KF1 of first robot R1 to control computer 37 of second robot R2, which thereupon computes the location of X-ray source RQ or the latter's X-ray source coordinate system KQ. It is also possible, however, for control computer 17 of first robot R1 to convey information about the location of X-ray source RQ, in particular the location of X-ray source coordinate system KQ, directly to control computer 37 of second robot R2.

In the described exemplary embodiments, X-ray source RQ is attached to first robot R1 and X-ray receiver RE is attached to second robot R2. It is also possible, however, for X-ray receiver RE to be attached to first robot R1 and for X-ray source RQ to be attached to second robot R2, i.e., for the robot to which X-ray receiver RE is attached to be the master.

The invention claimed is:

1. An X-ray device, comprising:
a first robot having a plurality of first articulation axes;
a second robot having a plurality of second articulation axes;
an X-ray source supported by one of said first and second robots;
an X-ray receiver supported by the other of said first and second robots;
a first controller controlling movement of said first robot about said first articulation axes; and
a second controller controlling movement of said second robot about said second articulation axes;
said first and second controllers operating in a master-slave configuration such that said second controller moves said second robot in response to movement of said first robot to maintain a predetermined distance and relative orientation between said X-ray source and said X-ray receiver.

2. The X-ray device of claim 1, wherein said first controller is configured to automatically move said first robot.

3. The X-ray device of claim 1, wherein said first controller is configured to permit manual positioning, by a user, of said X-ray source or said X-ray receiver supported on said first robot arm.

4. The X-ray device of claim 1, further comprising:
an input apparatus operatively coupled to said first controller, said first controller controlling movement of said first robot based on a manual entry received by said input apparatus.

5. The X-ray device of claim 1, further comprising:
a first attachment device on said first robot and supporting one of said X-ray source or said X-ray receiver; and
a second attachment device on said second robot and supporting the other of said X-ray source or said X-ray receiver;
wherein, during movement of said first robot arm, said first controller sends to said second controller information related to a position and an orientation of said first attachment device; and
wherein said second controller moves said second robot arm and said second attachment device based on: (a) a position and orientation of said second attachment device relative to said first attachment device, and (b) the information received from said first controller, such that said predetermined distance and relative orientation between said X-ray source and said X-ray receiver is maintained during movement of said first attachment device.

6. The X-ray device of claim 5, further comprising:
a first robot coordinate system associated with said first robot;
a second robot coordinate system associated with said second robot; and
a first attachment device coordinate system associated with said first attachment device;
wherein information sent by said first controller to said second controller includes position and orientation information about said first attachment device coordinate system during movement of said first robot arm; and
wherein said second controller moves said second robot and said second attachment device also based on: (c) the position and orientation of said first and second robot coordinate systems relative to one another, such that said predetermined distance and relative orientation between said X-ray source and said X-ray receiver is maintained during movement of said first attachment device.

7. The X-ray device of claim 5, wherein:
said first robot has a first basic coordinate system and said second robot has a second basic coordinate system,
said first X-ray source is supported by said first attachment device and has an X-ray source coordinate system,
said X-ray receiver is supported on said second attachment device and has a tool center point,
said first controller is configured, during movement of said first attachment device, to send information to said second controller associated with a position and an orientation of said X-ray source coordinate system, and
said second controller is configured to move said second attachment device based on (a) the information received from said first controller, and (b) the position and orientation of said first and second basic coordinate systems relative to one another, to orient said tool center point such that said predetermined distance and relative orientation between said X-ray source and said X-ray receiver is maintained during movement of said first attachment device.

8. The X-ray device of claim 1, wherein:
said first robot includes a first attachment device supporting one of said X-ray source or said X-ray receiver,
said second robot includes a second attachment device supporting the other of said X-ray source or said X-ray receiver,
said first controller is configured, during movement of said first attachment device, to send information to said second controller associated with a position and an orientation of said X-ray source or said X-ray receiver supported by said first attachment device, and
said second controller is configured to move said second attachment device in response to (a) a position and orientation of said second attachment device relative to said first attachment device and (b) the information received from said first controller, such that said predetermined distance and relative orientation between said X-ray source and said X-ray receiver is maintained during movement of said first attachment device.

9. The X-ray device of claim 8, wherein:
said first robot has a first basic coordinate system and said second robot has a second basic coordinate system,
said first attachment device has a first attachment device coordinate system,
the information sent by said first controller to said second controller includes information about the position and orientation of said first attachment device coordinate system, and
said second controller is further configured to move said second attachment device in response to (c) the position and orientation of said first and second basic coordinate systems relative to one another, such that said predetermined distance and relative orientation between said X-ray source and said X-ray receiver is maintained during movement of said first attachment device.

10. The X-ray device of claim 9, wherein:
said X-ray source is located on said first attachment device and has an X-ray source coordinate system,
said X-ray receiver is located on said second attachment device and has a tool center point,
said second controller accesses information associated with the relationship between said first attachment device coordinate system and said X-ray source coordinate system, and
said second controller directs movement of said second attachment device based on (a) the accessed information, (b) the position and orientation of said first attachment device coordinate system, and (c) the position and orientation of said first and second basic coordinate systems relative to one another, to orient said tool center point such that said predetermined distance and relative orientation between said X-ray source and said X-ray receiver is maintained during movement of said first attachment device.

11. The X-ray device of claim 9, wherein:
said X-ray receiver is located on said first attachment device and has an X-ray receiver coordinate system,
said X-ray source is located on said second attachment device and has a tool center point,
said second controller accesses information associated with the relationship between said first attachment device coordinate system and said X-ray receiver coordinate system, and
said second controller directs movement of said second attachment device based on (a) the accessed information, (b) the position and orientation of said first attachment device coordinate system, and (c) the position and orientation of said first and second basic coordinate systems relative to one another, to orient said tool center point such that said predetermined distance and relative orientation between said X-ray source and said X-ray receiver is maintained during movement of said first attachment device.

12. The X-ray device of claim 1, wherein:
said first robot has a first base mounted for linear motion thereof, and said second robot has a second base mounted for linear motion thereof.

13. A medical workstation comprising:
a first robot having a plurality of first articulation axes;
a second robot having a plurality of second articulation axes;
an X-ray source supported by one of said first and second robots;
an X-ray receiver supported by the other of said first and second robots;
a patient-transport trolley located between said X-ray source and said X-ray receiver;
a first controller controlling movement of said first robot about said first articulation axes; and
a second controller controlling movement of said second robot about said second articulation axes;
said first and second controllers operating in a master-slave configuration such that said second controller moves said second robot in response to movement of said first robot to maintain a predetermined distance and relative orientation between said X-ray source and said X-ray receiver.

* * * * *